(12) United States Patent
Park et al.

(10) Patent No.: US 9,579,167 B2
(45) Date of Patent: Feb. 28, 2017

(54) FIXTURE FOR A DENTAL IMPLANT AND AN IMPLANT SYSTEM COMPRISING THE SAME

(71) Applicant: MEGAGEN IMPLANT CO., LTD., Gyeongsan-si (KR)

(72) Inventors: Kwang Bum Park, Daegu (KR); Kyoung Ho Ryoo, Gwangju (KR); Kyu Seok Shon, Daegu (KR); June Ig Son, Daegu (KR)

(73) Assignee: MEGAGEN IMPLANT CO., LTD., Gyeongsan-si (KR)

( * ) Notice: Subject to any disclaimer, the term of this patent is extended or adjusted under 35 U.S.C. 154(b) by 0 days.

(21) Appl. No.: 14/877,176

(22) Filed: Oct. 7, 2015

(65) Prior Publication Data

US 2016/0022384 A1    Jan. 28, 2016

Related U.S. Application Data

(63) Continuation-in-part of application No. 13/642,570, filed as application No. PCT/KR2010/009603 on Dec. 30, 2010.

(30) Foreign Application Priority Data

Apr. 22, 2010  (KR) .......................... 10-2010-0037567

(51) Int. Cl.
*A61C 8/00*   (2006.01)
(52) U.S. Cl.
CPC ............ *A61C 8/0022* (2013.01); *A61C 8/006* (2013.01); *A61C 8/0068* (2013.01); *A61C 8/0071* (2013.01)
(58) Field of Classification Search
CPC ... A61C 8/0022; A61C 8/0018; A61C 8/0068; A61C 8/0075; A61C 8/0092
(Continued)

(56) References Cited

U.S. PATENT DOCUMENTS 5,116,225 A  *  5/1992  Riera ..................... A61C 8/005
                                                             433/173
5,199,873 A     4/1993  Schulte et al.
(Continued)

FOREIGN PATENT DOCUMENTS

EP         0438048       7/1991
ES         2171112       8/2002
(Continued)

OTHER PUBLICATIONS

European Office Action—European Application No. 13173577.1 issued on Nov. 11, 2015, citing ES 2 171 112, US 2005/250074, WO 2009/071712, U.S. Pat. No. 6,315,564, JP 2008 245994, KR 200 429 575, EP 0 438 048 and US 2009/280454.
(Continued)

*Primary Examiner* — Matthew Nelson
(74) *Attorney, Agent, or Firm* — Cantor Colburn LLP

(57) ABSTRACT

A dental implant fixture comprises: a body; a continuous thread part including a continuous thread continuously formed in a spiral shape along an outer circumferential direction of the body; a bone damage prevention part formed at one end portion of the body and preventing an alveolar bone existing in an opening area of a hole where the body is implanted from being damaged due to the continuous thread part; and an entrance guide part provided at the other end portion of the body and guiding the body in an initial implantation entrance direction. The entrance guide part comprises; a flat portion of horizontal flat; an inclined portion extending upward from a circumferential surface of the flat portion with an upwardly increasing radius; and a rounded portion connecting the inclined portion and the continuous thread part and having at least one area inwardly rounded toward the centerline of the fixture.

6 Claims, 7 Drawing Sheets

(58) Field of Classification Search
USPC .................................................. 433/172–176
See application file for complete search history.

(56) References Cited

U.S. PATENT DOCUMENTS

| | | | | |
|---|---|---|---|---|
| 5,209,659 | A * | 5/1993 | Friedman | A61C 8/0018 433/173 |
| 5,342,199 | A * | 8/1994 | Gillespie | A61C 8/0018 433/173 |
| 5,564,923 | A * | 10/1996 | Grassi | A61C 8/0018 433/173 |
| 5,642,996 | A * | 7/1997 | Mochida | A61C 8/0022 433/174 |
| 6,149,432 | A * | 11/2000 | Shaw | A61C 8/0022 433/174 |
| 6,203,324 | B1 * | 3/2001 | Wils | A61C 8/0022 433/173 |
| 6,315,564 | B1 | 11/2001 | Levisman | |
| 6,406,296 | B1 * | 6/2002 | Hollander | A61C 8/0022 433/174 |
| 6,419,489 | B1 * | 7/2002 | Jorneus | A61C 8/0022 433/141 |
| 6,846,180 | B1 * | 1/2005 | Joos | A61C 8/0022 433/174 |
| 6,939,135 | B2 * | 9/2005 | Sapian | A61C 8/005 433/174 |
| 7,677,891 | B2 * | 3/2010 | Niznick | A61C 8/0025 433/174 |
| 2005/0250074 | A1 * | 11/2005 | Lang | A61B 17/1615 433/174 |
| 2006/0292524 | A1 * | 12/2006 | Lorenzon | A61C 8/0018 433/174 |
| 2007/0037122 | A1 * | 2/2007 | Bassett | A61C 8/0001 433/173 |
| 2007/0184673 | A1 * | 8/2007 | Park | A61C 8/0022 439/15 |
| 2008/0261174 | A1 * | 10/2008 | Gittleman | A61C 8/0048 433/172 |
| 2008/0261176 | A1 * | 10/2008 | Hurson | A61C 8/0022 433/174 |
| 2009/0142732 | A1 * | 6/2009 | Kahdemann | A61C 8/0069 433/174 |
| 2009/0280454 | A1 * | 11/2009 | Hanna | A61C 8/0018 433/174 |
| 2009/0325126 | A1 * | 12/2009 | Fromovich | A61C 8/0022 433/174 |
| 2010/0112523 | A1 * | 5/2010 | Fromovich | A61C 8/0022 433/174 |
| 2010/0119993 | A1 * | 5/2010 | Schulter | A61C 8/0066 433/173 |
| 2010/0143869 | A1 * | 6/2010 | Padros Fradera | A61C 8/005 433/174 |
| 2010/0143870 | A1 * | 6/2010 | Kahdemann | A61C 8/0012 433/174 |
| 2010/0233656 | A1 * | 9/2010 | Garcia Saban | A61C 8/0001 433/173 |
| 2010/0291507 | A1 * | 11/2010 | Abdelgany | A61C 8/005 433/174 |
| 2010/0330530 | A1 * | 12/2010 | Menzel | A61C 8/0018 433/173 |

FOREIGN PATENT DOCUMENTS

| | | |
|---|---|---|
| FR | 2915085 | 10/2008 |
| JP | H07253109 | 10/1995 |
| JP | 07313529 | 12/1995 |
| JP | 08019555 | 1/1996 |
| JP | 09042257 | 2/1997 |
| JP | 2000512884 | 10/2000 |
| JP | 2002527188 | 8/2002 |
| JP | 2003513684 | 4/2003 |
| JP | 2006296558 | 11/2006 |
| JP | 2007135751 | 6/2007 |
| JP | 2008529572 | 8/2008 |
| JP | 2008245994 | 10/2008 |
| KR | 200416306 | 5/2006 |
| KR | 200429575 | 10/2006 |
| KR | 1020080033221 | 4/2008 |
| KR | 1020100022898 | 3/2010 |
| WO | 2009071712 | 6/2009 |
| WO | 2009097218 | 8/2009 |

OTHER PUBLICATIONS

European Search Report—European Application No. 131735771.1 issued on Jan. 17, 2014, citing ES 2 171 112, US 2005/250074, WO 2009/071712 and U.S. Pat. No. 6,315,564.
International Search Report—PCT/KR2010/009603 dated Sep. 30, 2011.

* cited by examiner

FIXTURE FOR A DENTAL IMPLANT AND AN IMPLANT SYSTEM COMPRISING THE SAME

CROSS REFERENCE TO RELATED APPLICATIONS

This application is a continuation-in-part application of U.S. application Ser. No. 13/642,570, filed on Oct. 22, 2012, which is a National Stage of International Application No. PCT/KR2010/009603, filed on Dec. 30, 2010, which claims priority to and the benefit of Korean Application No. 10-2010-0037567, filed on Apr. 22, 2010, in the Korean Intellectual Property Office, the entire contents of which are incorporated herein by reference.

TECHNICAL FIELD

The present disclosure relates to a dental implant fixture and an implant system having the same, and more particularly, to an implant system with which an implant surgery may be conveniently performed because another fixture may be used without additional drilling when implantation of a first fixture fails.

BACKGROUND ART

In principle, an implant means a substitute configured to restore damaged human tissue. However, in dentistry, an implant means a series of medical procedures for implanting an artificial tooth. In the medical procedures, a fixture, which is a dental root formed of such rejection-free material as titanium to replace a damaged dental root, is implanted into an alveolar bone where a tooth was pulled out, and then a dental implant is fixed to restore functions of the tooth.

Typical prostheses or dentures may hurt adjacent teeth and bones with time. However, an implant does not hurt adjacent tooth tissue, and may be used semi-permanently since it causes no tooth decay while having the same function and shape as a natural tooth.

In the medical procedures, also referred to as an implant or implant procedures, a designated drill is used to bore a hole at an implant location, and then a fixture is implanted into and osteointegrated with an alveolar bone, although the procedures may be different depending upon a variety of types of the fixture. Then, in general, an abutment is coupled with the fixture, and a finishing prosthesis is applied to the abutment to finish the procedures.

An implant may restore a single missing tooth, increase the functions of the dentures of a patient with partial or complete anodontia, improve the appearance of a dental prosthesis, disperse the excessive stress upon adjacent supporting bone tissue, and help stabilize a set of teeth.

In general, such an implant includes a fixture which is an artificial dental root to be implanted, an abutment coupled with the fixture, an abutment screw fixing the abutment to the fixture, and an artificial tooth coupled with the abutment. Here, a healing abutment (not shown) may be coupled with the fixture to maintain the coupled state before the abutment is coupled with the fixture, i.e., until the fixture is osteointegrated with an alveolar bone.

A fixture, which is a part of an implant, is implanted into a drilled hole in an alveolar bone where the medical procedures are to be applied, and acts as an artificial dental root. Therefore, a fixture needs to be firmly implanted in the alveolar bone.

Thus, a thread part (thread) may be disposed on the outer surface of a fixture so that the fixture is firmly coupled with the inner sidewall of an alveolar bone where a drilled hole is formed. The thread part is led into the alveolar bone so that the fixture and the alveolar bone are firmly coupled with each other, and strengthens the force with which the fixture fixes the alveolar bone by increasing the contact area of both.

Meanwhile, as described above, an implant surgery is carried out by forming a hole with a drill in an alveolar bone, implanting a fixture in the hole, coupling the fixture with an abutment when osteointegration progresses, and then applying an artificial tooth to finish the procedures. In such an implant surgery, fixtures with different sizes (maximum thread diameters) may be used depending upon operation conditions. Then, different drills need to be used. Usually, a large-scale drill is used for a large fixture, and a small-scale drill is used for a small fixture since the bodies of the fixtures vary depending on the sizes of the fixtures.

However, a cumbersome operation may be entailed when a drill corresponding to the size of a fixture needs to be selected, or when an additional boring is required for implanting a larger fixture with a hole for fixture implanting already formed in an alveolar bone. Especially, when another fixture is implanted after an initial implanting failed, an additional boring with an additional drill is necessary since the sizes of the bodies of the fixtures are different. Therefore, the development of a new implant system is required for more convenient implant procedures.

On the other hand, in a typical conventional dental implant fixture, a certain section of a thread part is discontinued, that is, the thread part does not continue, and a cutting edge portion is formed in the discontinued area to make a fixture easily implanted. However, the cutting edge portion formed by discontinuing the thread part may misalign the fixture with a desired implantation direction and thus a solution for this issue is needed.

Also, in the conventional dental implant fixture, since the thread part is formed across the entire area of an outer surface of a body of the fixture, when an entrance of a hole is relatively narrow, for example, a bone (an alveolar bone) existing in an opening area of the hole may be damaged due to the thread part formed in the entire area of the outer surface of the body. As a result, an implant surgery may fail and thus a solution for this issue is needed.

SUMMARY OF THE INVENTION

The present invention provides an implant system with which an implant surgery may be conveniently performed because another fixture having a different size may be used without additional drilling when implantation of a first fixture fails.

The present invention also provides a dental implant fixture which may prevent misalignment of a fixture with a desired direction of fixture implantation due to a cutting edge portion formed in a conventional fixture, leading a successful implant surgery, and an implant system having the same.

The present invention also provides a dental implant fixture which may prevent damage of an alveolar bone existing in an opening area of a hole, in which a fixture is implanted, due to a thread part formed across the entire area of an outer surface of a body as in a conventional fixture, leading a successful implant surgery, and an implant system having the same.

According to an aspect of the present invention, there is provided an implant system including a first fixture comprising a first body and a first continuous thread part, the first continuous thread part having a spiral shape and formed on an outer circumferential surface of the first body; and a second fixture comprising a second body and a second continuous thread part, the second body having the same shape and standard as those of the first body, the second continuous thread part having a spiral shape and formed on an outer circumferential surface of the second body, wherein a diameter of the second continuous thread part is different from a diameter of the first continuous thread part.

An end portion region of the second continuous thread part may be extended further outwardly in a radius direction from a leading end portion of the first continuous thread part by a predetermined length.

The end portion region of the second continuous thread part may be extended further outwardly in a radius direction from a leading end portion of the first continuous thread part by a predetermined length identically to an upper curved surface and a lower curved surface of the first continuous thread part.

The first fixture may further include a first bone damage prevention part formed at one end portion of the first body and preventing an alveolar bone existing in an opening area of a hole where the first fixture is implanted from being damaged due to the first continuous thread part; and the second fixture may further include a second bone damage prevention part formed at one end portion of the second body and preventing the alveolar bone existing in the opening area of the hole from being damaged due to the second continuous thread part The first and second bone damage prevention parts may be respectively provided in non-threaded regions where the first and second continuous thread parts are not formed at outer surfaces of end portions of the first and second bodies and integrally formed in the first and second bodies by a predetermined length in the one end portion of each the first and second bodies.

Each of the first and second bone damage prevention parts may have a non-linear outer surface such that a diameter of each of the first and second bone damage prevention parts decreases from one end portion of each of the first and second bodies to an opposite side thereof.

The first and second bodies may be provided such that an outside of each of the first and second bodies is tapered in a manner such that a diameter of each of the first and second bodies deceases along an implantation direction; and an imaginary contour line connecting leading end portions of the first and second continuous thread parts forms a taper inclination line such that a width between the imaginary contour lines gradually decreases in the implantation direction.

A pitch between threads of the first continuous thread part and a pitch between threads of the second continuous thread part may be identical to each other.

Each of the first and second continuous thread parts may include a leading end portion that is vertical or inclined toward one side; and a curved part formed on an upper or lower surface of the leading end portion and reducing resistance torque, wherein the first fixture further comprises a first entrance guide part provided at the other end portion of the first body opposite to the first bone damage prevention part, and formed as long as a predetermined section in a lengthwise direction of the first body from the leading end portion of the first body with respect to a direction in which the first body is implanted and guiding the first body in an initial implantation entrance direction, and the second fixture further comprises a second entrance guide part provided at the other end portion of the second body opposite to the second bone damage prevention part, and formed as long as a predetermined section in a lengthwise direction of the second body from the leading end portion of the second body with respect to a direction in which the second body is implanted and guiding the second body in an initial implantation entrance direction, According to another aspect of the present invention, there is provided an implant system including a first fixture comprising a first body and a first bone damage prevention part formed at one end portion of the first body and preventing an alveolar bone existing in an opening area of a hole where the first fixture is implanted from being damaged; and a second fixture comprising a second body that is the same as the first body and a second bone damage prevention part formed at one end portion of the second body and preventing the alveolar bone existing in the opening area of the hole from being damaged.

The first fixture may include a first thread part formed in a spiral shape along an outer circumferential direction of the first body, the second fixture may include a second thread part formed in a spiral shape along an outer circumferential direction of the second body, and an end portion region of the second thread part may be extended further outwardly in a radius direction from a leading end portion of the first thread part by a predetermined length.

The end portion region of the second thread part may be extended further outwardly in a radius direction from a leading end portion of the first thread part by a predetermined length identically to an upper curved surface and a lower curved surface of the first thread part.

The first and second bodies may be provided such that an outside of each of the first and second bodies is tapered in a manner such that a diameter of each of the first and second bodies gradually deceases along an implantation direction, and an imaginary contour line connecting leading end portions of the first and second thread parts forms a taper inclination line such that a width between the imaginary contour lines gradually decreases in the implantation direction.

A pitch between threads of the first thread part and a pitch between threads of the second thread part may be identical to each other, and the first and second thread parts may respectively be first and second continuous thread parts that are continuously formed on the first and second bodies.

Each of the first and second bone damage prevention parts may be formed in a non-threaded region of an outer surface of one end portion of each of the first and second bodies and integrally formed in the first and second bodies by a predetermined length in the one end portion of each o the first and second bodies Each of the first and second bone damage prevention parts may have a non-linear outer surface such that a diameter of each of the first and second bone damage prevention parts decreases from one end portion of each of the first and second bodies to an opposite side thereof.

According to another aspect of the present invention, there is provided a dental implant fixture including a body: and a continuous thread part continuously formed in a spiral shape along an outer circumferential direction of the body.

The dental implant fixture may further include a bone damage prevention part formed at one end portion of the body and preventing an alveolar bone existing in an opening area of a hole where the dental implant fixture is implanted from being damaged due to the continuous thread part.

The bone damage prevention part may be provided in a non-threaded region where the continuous thread part is not formed at an outer surface of an end portion of the body and integrally formed in the body by a predetermined length in the one end portion of the body.

The bone damage prevention part may be integrally formed in the body by a predetermined length at one end portion of the body.

The bone damage prevention part may have a non-linear outer surface such that a diameter of the bone damage prevention part decreases from one end portion of the body to an opposite side thereof.

The dental implant fixture may further include an entrance guide part provided at the other end portion of the body opposite to the bone damage prevention part, and formed as long as a predetermined section in a lengthwise direction of the body from the leading end portion of the body with respect to a direction in which the body is implanted and guiding the body in an initial implantation entrance direction The body may be provided such that an outside of the body is tapered in a manner such that a diameter of the body deceases along an implantation direction, and an imaginary contour line connecting a leading end portion of the continuous thread part forms a taper inclination line such that a width between the imaginary contour lines gradually decreases in the implantation direction.

The continuous thread part may include a leading end portion that is vertical or inclined toward one side; and a curved part formed on an upper or lower surface of the leading end portion and reducing resistance torque, wherein the curved part is an upper or lower curved part respectively formed on an upper or lower surface with respect to the leading end portion.

An abutment coupling part to which an abutment is coupled may be provided in an inner area of one end portion of the body, and the abutment coupling part may includes: a first recessed part primarily recessed from one end of the body in a length direction of the body; a second recessed part secondarily recessed deeper from the other end of the first recessed part in the length direction of the body and has a polygonal shape; and a screw hole formed in a center region of the second recessed part in the length direction of the body, to which an abutment screw for coupling with the abutment is coupled.

According to another aspect of the present invention, there is provided a dental implant fixture including a body; and a bone damage prevention part preventing an alveolar bone existing in an opening area of a hole where the body is implanted.

The bone damage prevention part may be provided in a non-threaded region at an outer surface of an end portion of the body and integrally formed in the body by a predetermined length in the one end portion of the body.

The bone damage prevention part may have a non-linear outer surface such that a diameter of the bone damage prevention part decreases from one end portion of the body to an opposite side thereof.

An abutment coupling part to which an abutment is coupled may be provided in an inner area of one end portion of the body, and the abutment coupling part may include: a first recessed part primarily recessed from one end of the body in a length direction of the body; a second recessed part secondarily recessed deeper from the other end of the first recessed part in the length direction of the body and has a polygonal shape; and a screw hole formed in a center region of the second recessed part in the length direction of the body, to which an abutment screw for coupling with the abutment is coupled.

According to another aspect of the present invention, there is provided a dental implant fixture comprising: a body; a continuous thread part including a continuous thread continuously formed in a spiral shape along an outer circumferential direction of the body; a bone damage prevention part formed at one end portion of the body and preventing an alveolar bone existing in an opening area of a hole where the body is implanted from being damaged due to the continuous thread part; and an entrance guide part provided at the other end portion of the body and guiding the body in an initial implantation entrance direction.

The entrance guide part comprises: a flat portion which is horizontal flat; an inclined portion extending upward from a circumferential surface of the flat portion with an upwardly increasing radius; and a rounded portion connecting the inclined portion and the continuous thread part and having at least one area inwardly rounded toward the centerline of the fixture.

The bone damage prevention part is provided in a non-threaded region where the continuous thread part is not formed at an outer surface of an end portion of the body.

The bone damage prevention part is integrally formed in the body by a predetermined length at one end portion of the body.

The bone damage prevention part has a non-linear outer surface extending to a starting point of the continuous thread part, and has a diameter gradually decreasing along an implantation direction.

The body is provided such that an outside of the body is tapered in a manner such that a diameter of the body deceases along an implantation direction, and an imaginary contour line connecting a leading end portion of the continuous thread forms a taper inclination line such that a width between the imaginary contour lines gradually decreases in the implantation direction.

The continuous thread comprises: a leading end portion that is vertical or inclined toward one side; and a curved part formed on an upper or lower surface of the leading end portion and reducing resistance torque.

The curved part is an upper or lower curved part respectively formed on an upper or lower surface with respect to the leading end portion.

An abutment coupling part to which an abutment is coupled is provided in an inner area of one end portion of the body, and the abutment coupling part comprises: a first recessed part primarily recessed from one end of the body in a length direction of the body; a second recessed part secondarily recessed deeper from the other end of the first recessed part in the length direction of the body and has a polygonal shape; and a screw hole formed in a center region of the second recessed part in the length direction of the body, to which an abutment screw for coupling with the abutment is coupled.

According to the embodiments, although implantation of the first fixture fails, the second fixture may be directly implanted without additional drilling. Therefore, an implant surgery may be performed more easily as compared with the related art.

Also, according to the embodiments, the misalignment of a fixture with a desired direction of fixture implantation due to a cutting edge portion formed in a conventional fixture may be prevented, leading a successful implant surgery.

In addition, according to the embodiments, the damage of an alveolar bone existing in an opening area of a hole, in which a fixture is implanted, due to a thread part formed across the entire area of an outer surface of a body as in a conventional fixture may be prevented, leading a successful implant surgery.

DETAILED DESCRIPTION OF THE INVENTION

In the following detailed description of the preferred embodiments, reference is made to the accompanying drawings that form a part hereof, and in which is shown by way of illustration specific preferred embodiments in which the invention may be practiced. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the invention, the description may omit certain information known to those skilled in the art. The following detailed description is, therefore, not to be taken in a limiting sense, and the scope of the present invention is defined only by the appended claims.

Figure 1:
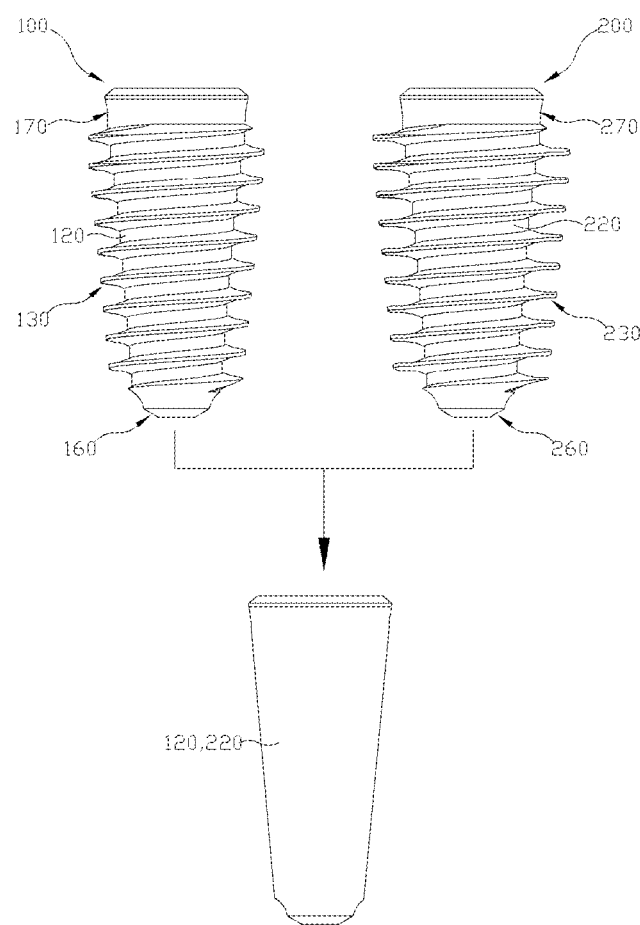
FIG. 1 is a schematic structural view of an implant system according to an embodiment of the present invention.
Figure 2:
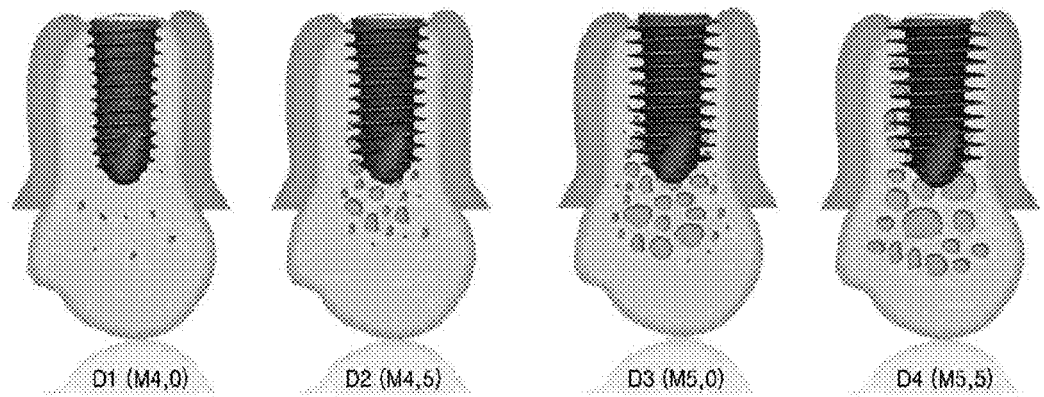
FIG. 2 is an image illustrating states in which four fixtures having different sizes are implanted in a hole of an alveolar bone of the same diameter.
Figure 3:
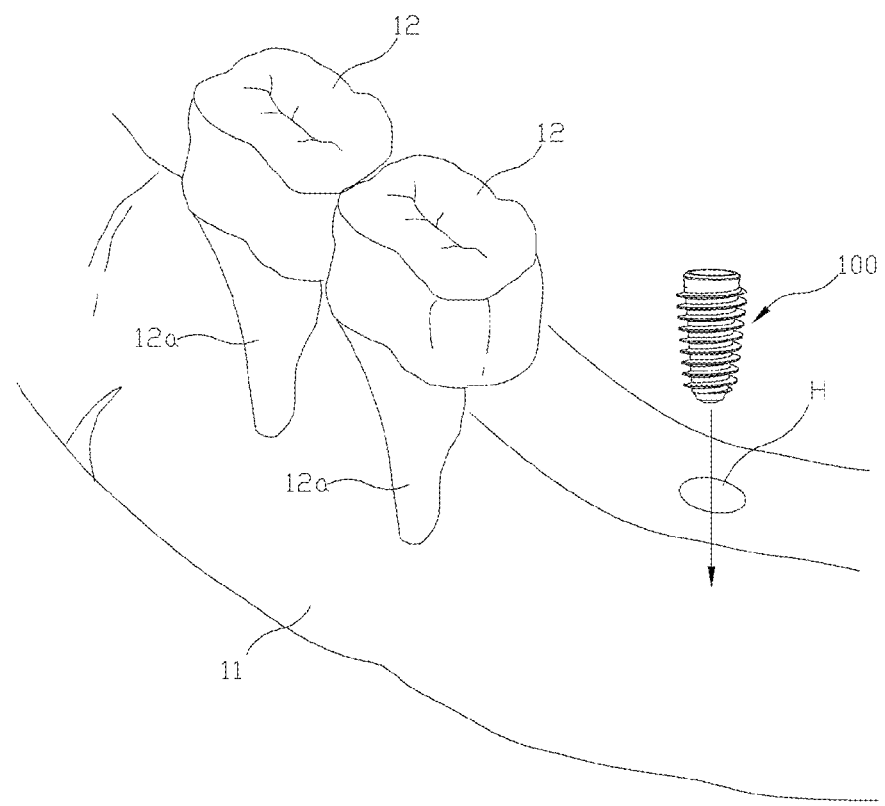
FIG. 3 is a perspective view schematically illustrating a process of implanting the first fixture of the dental implant of FIG. 1.
Figure 4:
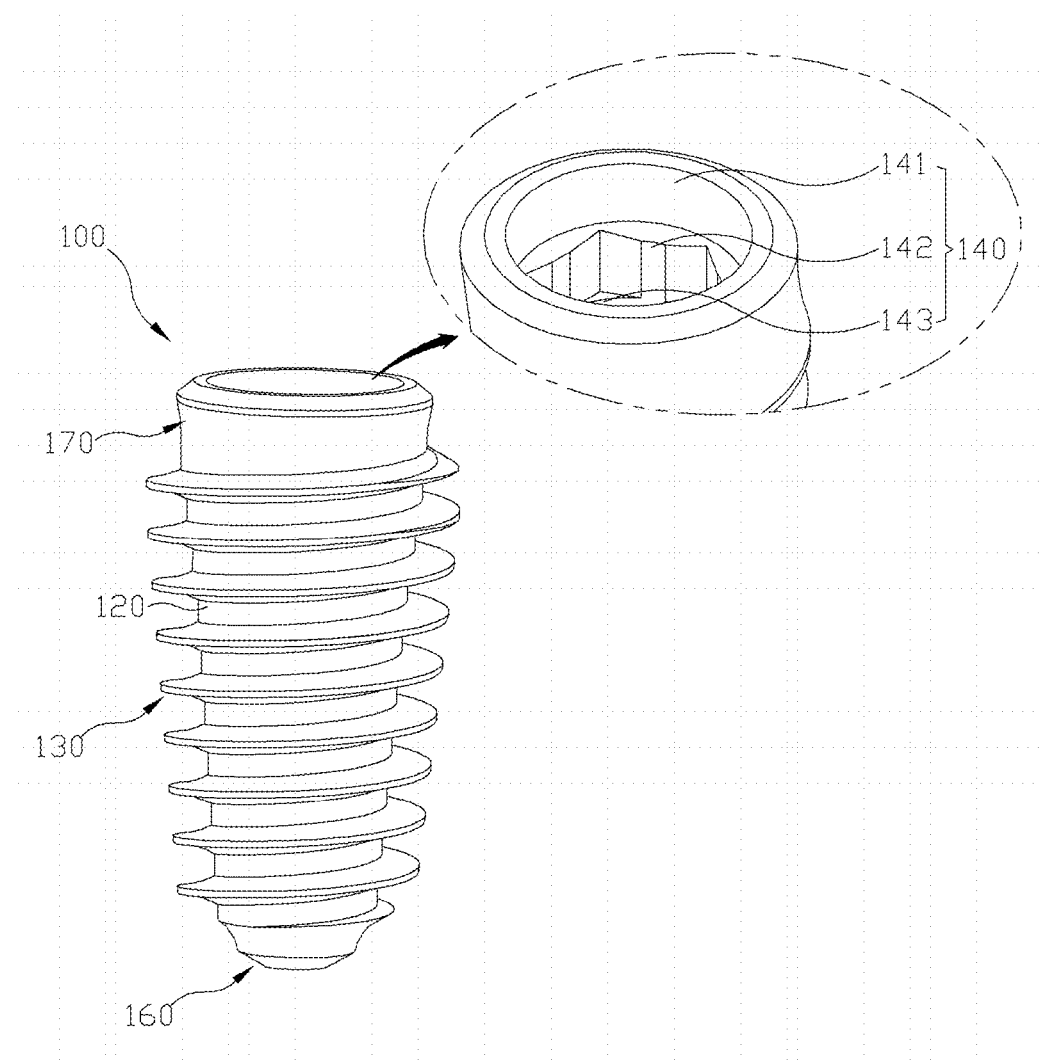
FIGS. 4 through 7 are respectively a perspective view, a side view, a cross-sectional view, and a plan view of the first fixture.
Figure 5:
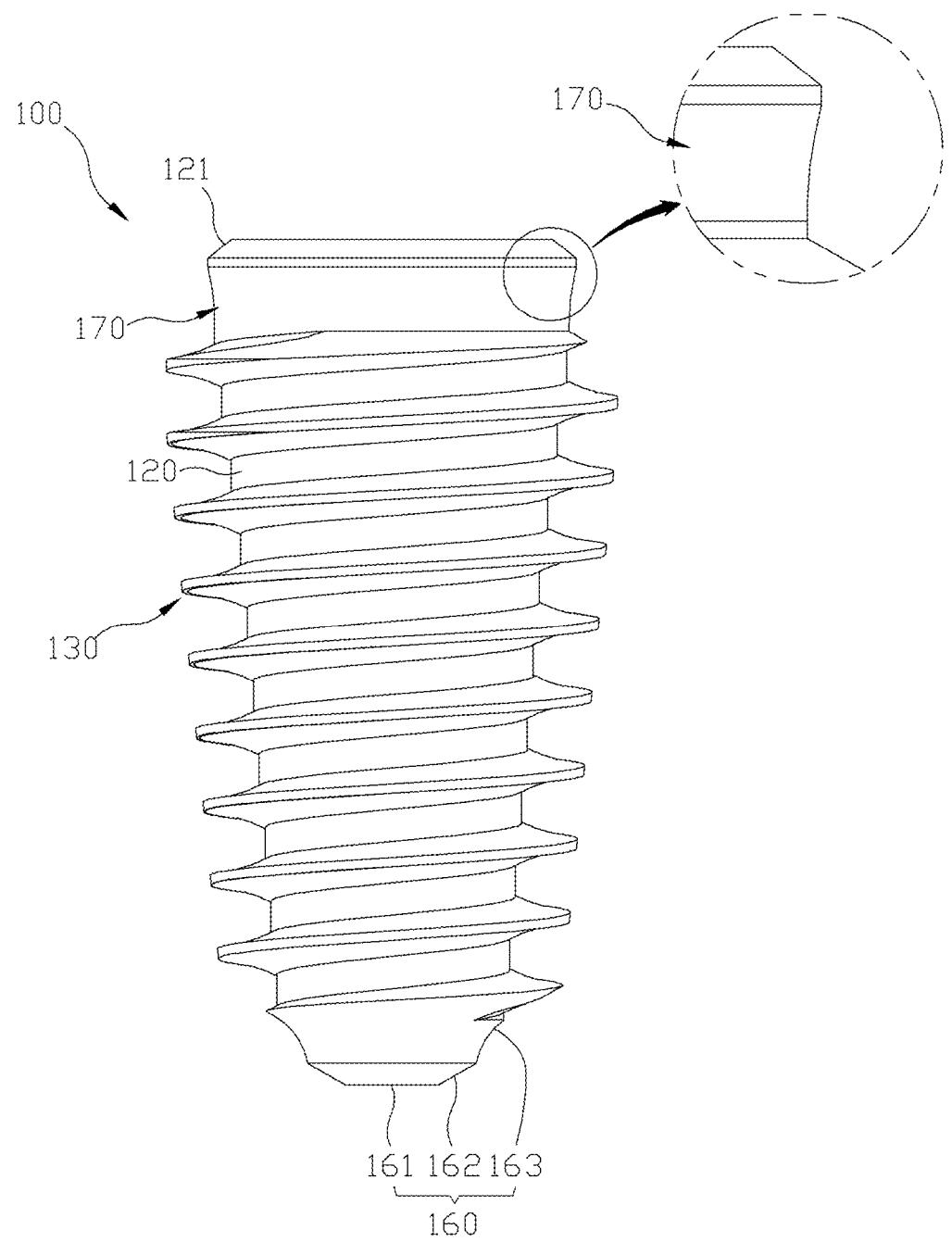
Figure 6:
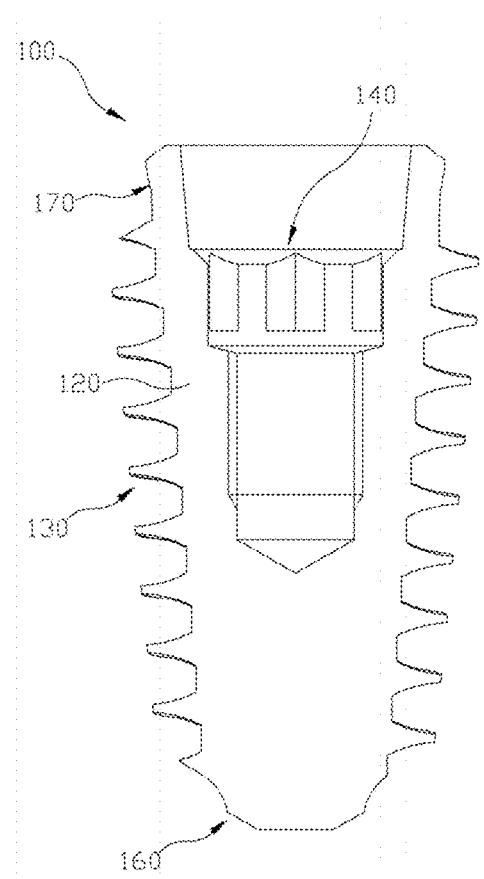
Figure 7:
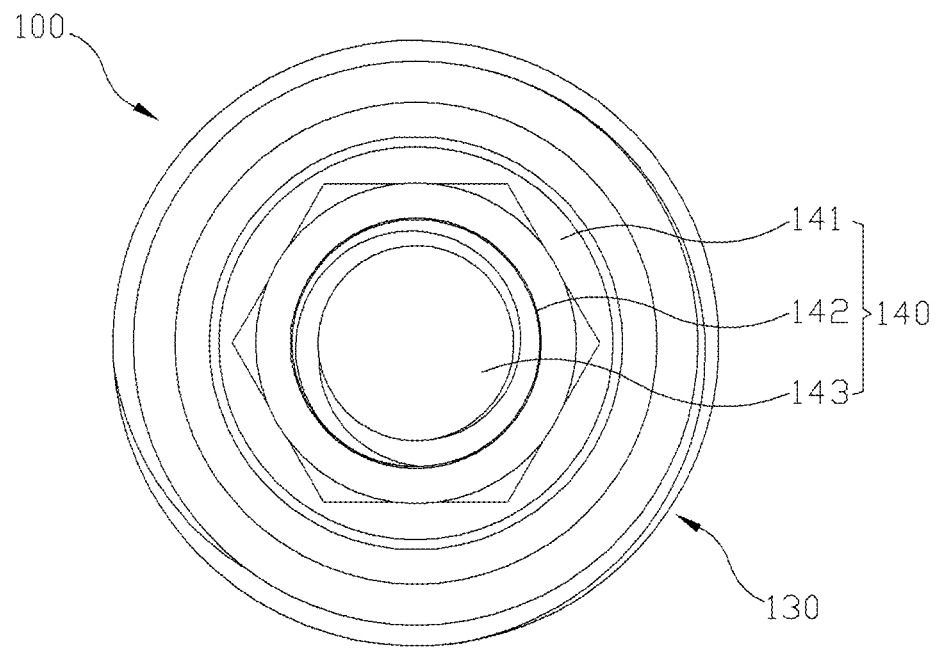

FIG. 1 is a schematic structural view of an implant system according to an embodiment of the present invention. FIG. 2 is an image illustrating states in which four fixtures having different sizes are implanted in a hole of an alveolar bone of the same diameter. FIG. 3 is a perspective view schematically illustrating a process of implanting the first fixture of the dental implant of FIG. 1.

Referring to FIG. 3 first, a plurality of teeth 12 are arranged along a gum 11. The teeth 12 are primary digestive means that break food into small pieces before the food is sent to the stomach. Usually, people have twenty eight teeth.

If one of the teeth 12 is lost (for example, a molar is lost), it is not good for the appearance, as well as it is difficult to chew. Thus, a first fixture 100 may be implanted in the gum 11 as a substitute for a dental root 12a of the lost tooth 12. If the size of the first fixture 100 is not suitable, a second fixture 200 may be implanted. The first fixture 100 and the second fixture 200 may be formed of titanium (Ti) or a titanium (Ti) alloy that the human body does not reject.

In this way, the first fixture 100 or the second fixture 200, whatever selected as necessary, may be implanted in an alveolar bone inside the gum 11. Drilling is carried out for the initial implantation of the first fixture 100. That is a drill hole H is formed in the alveolar bone at a predetermined position.

An implant system according to an embodiment of the present invention is described below with reference to FIGS. 1 and 2. The implant system according to the present embodiment generally includes two fixtures: a first fixture 100 and a second fixture 200.

As described above, the first fixture 100 is implanted in the drill hole H (refer to FIG. 3) formed in an alveolar bone and the second fixture 200 is implanted in the same hole by pulling out the first fixture 100 when the first fixture 100 is too large for the hole. Of course, a third fixture (not shown), a fourth fixture (not shown), etc. having relatively larger sizes than the second fixture 200 may be implanted in the drill hole H under the same conditions.

In order for the second fixture 200 to be implanted in the same place where the first fixture 100 is implanted without additional drilling and also without damaging an alveolar bone therearound, the first and second fixtures 100 and 200 may have the conditions in common. As such, in the implant system according to the present embodiment, the first and second fixtures 100 and 200 have the same structure except for some portions. Thus, in the following descriptions, while a description about the structure of the second fixture 200 is largely omitted, the structure of the first fixture 100 is mainly described in detail with differences between the first and second fixtures 100 and 200 as necessary.

For reference, the first fixture 100 that is described below may be one used for an initial implant surgery or may be for emergency use when the first fixture 100 is directly implanted in an alveolar bone without filling a damaged portion without a predetermined bone substitute material when a surgery fails. This condition also applies to the second fixture 200.

Figure 8:
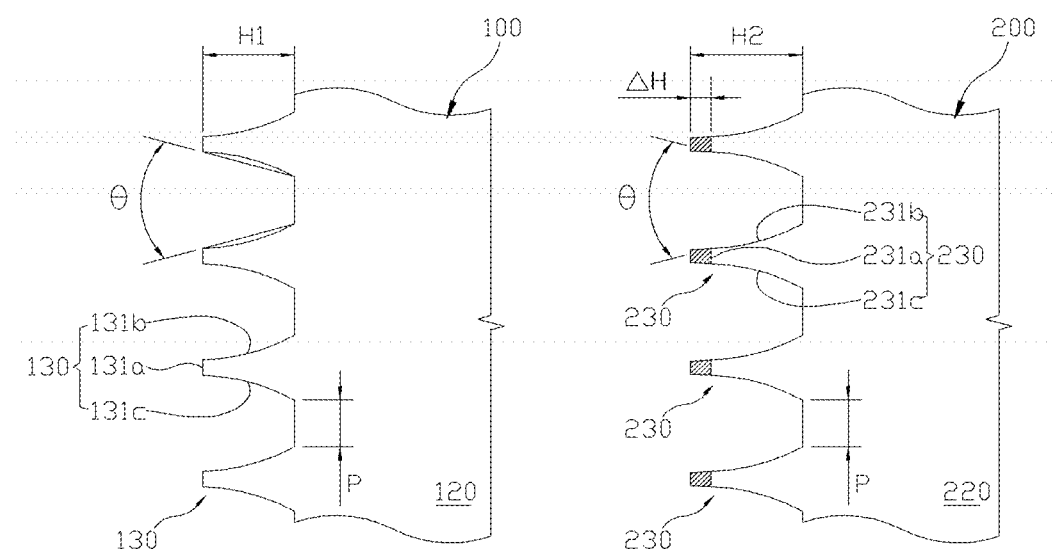
FIG. 8 is a partial enlarged view illustrating a continuous thread part of each of the first and second fixtures.
Figure 9:
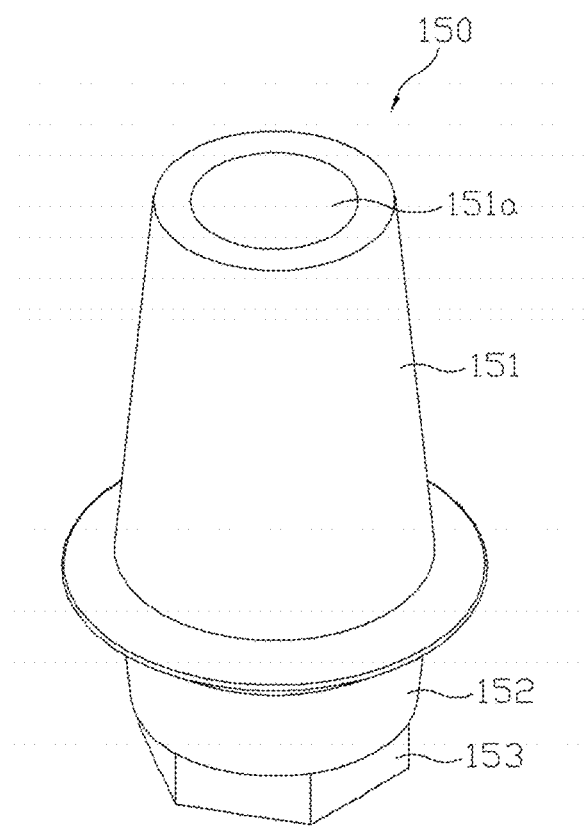
FIG. 9 is a perspective view illustrating an abutment to be coupled to the first fixture according to an embodiment.

FIGS. 4 through 7 are respectively a perspective view, a side view, a cross-sectional view, and a plan view of the first fixture. FIG. 8 is a partial enlarged view illustrating a continuous thread part of each of the first and second fixtures. FIG. 9 is a perspective view illustrating an abutment to be coupled to the first fixture according to an embodiment.

Referring to FIGS. 1 and 4 through 9, the first fixture 100 for a dental implant as a part of the implant system of the present embodiment includes a first body 120 having a first bone damage prevention part 170 and a first entrance guide part 160 formed at the opposite ends thereof and a first continuous thread part 130 formed in a spiral shape on the outer circumferential surface of the first body 120 to be continuously.

For reference, as illustrated in FIG. 1, like the first fixture 100, the second fixture 200 for a dental implant as another part of the implant system of the present embodiment also includes a second body 220 having a second bone damage prevention part 270 and a second entrance guide part 260 formed at the opposite ends thereof and a second continuous thread part 230 formed in a spiral shape on the outer circumferential surface of the second body 220 to be continuously. The first and second bodies 120 and 220 may be provided to have substantially the same size.

First, the first body 120 constitutes a central stem of the first fixture 100 of the present embodiment. Since the first fixture 100 is implanted in the direction of an arrow of FIG. 3, the outside of the first body 120 is tapered in a manner such that the diameter of the first body 120 deceases along an implantation direction. This condition commonly applied to the second body 220 of the second fixture 200.

In the related art, a body of a fixture (not shown) has a cylindrical shape having a uniform diameter. However, in the present embodiment, each of the bodies 120 and 220 of the first and second fixtures 100 and 200 is partially tapered in a manner such that the diameter of the first body 120 decreases along the implantation direction, thereby facilitating implantation. The first and second bodies 120 and 220 may have the same inclination throughout the entire area of the outer surface thereof or a tapered inclination only in a particular section. In the latter case, a tapered inclination applies to a section from the top end of each of the first and second bodies 120 and 220 to a middle portion thereof in FIG. 1, whereas the other part may have a linear shape like a cylinder. In this case, initial implantation is made easy and a strong fixing force may be provided.

A bevel part 121 is formed at an edge area of one end of the first body 120. The bevel part 121 provides a relatively large contact area than an alveolar bone and thus a strong fixing force is provided. Also, a first abutment coupling part 140, to which an abutment 150 (refer to FIG. 9) is coupled, is provided in an inner area of one end portion of the first body 120 where the first bevel part 121 is formed.

With reference to FIG. 9, the abutment 150 will now be described briefly. The abutment 150 has a truncated cone shape. The abutment 150 includes an abutment body 151 through which a penetration hole 151a is formed, a first coupling part 152 disposed at a lower end of the abutment body 151, and a second coupling part 153 disposed at a lower end of the first coupling part 152. The first coupling part 152 may be fitted into a first recessed part 141 (described later) of the first abutment coupling part 140, and the second coupling part 153 may be fitted into a second recessed part 142 (described later) of the first abutment coupling part 140.

Since the first recessed part 141 has a tapered inner wall as described below, the outer surface of the first coupling part 152 of the abutment 150 is also tapered. The second coupling part 153 has a shape corresponding to the shape of the second recessed part 142.

In detail, the first abutment coupling part 140 to which the abutment 150 is coupled includes the first recessed part 141, the second recessed part 142, and a screw hole 143. The first recessed part 141 is primarily recessed from one end of the first body 120 in the length direction of the first body 120. The second recessed part 142 is secondarily recessed deeper from the other end of the first recessed part 141 in the length direction of the first body 120 and has a hexagon shape. The screw hole 143 is formed in a center region of the second recessed part 142 in the length direction of the first body 120. An abutment screw (not shown) is coupled to the screw hole 143 for coupling with the abutment 150.

The first recessed part 141 is coupled with the first coupling part 152 of the abutment 150 (refer to FIG. 9). At this time, it may be necessary to bring the first coupling part 152 of the abutment 150 into strong or tight contact with the first recessed part 141 of the first fixture 100. This is to prevent detachment and guarantee sealing for avoiding infection. The inner wall of the first recessed part 141 is tapered downwardly so that the diameter of the inner wall decreases from the upper side to the lower side. Like the inclined angle of the outer surface of the first coupling part 152 of the abutment 150, the inclined angle of the inner wall of the first recessed part 141 may be in the range from 2 degrees to 6 degrees. If the inclined angle of the inner wall of the first recessed part 141 is in the above-mentioned angle range, when the abutment 150 is coupled to the first fixture 100, the first coupling part 152 of the abutment 150 may be securely or tightly coupled to the to the first recessed part 141.

The second coupling part 153 of the abutment 150 passing through the first recessed part 141 is coupled to the second recessed part 142 with shape matching. As shown in FIG. 9, if the second coupling part 153 of the abutment 150 has, for example, a hexagonal nut shape, the second recessed part 142 may also be formed into a hexagonal shape to have a matching shape. That is, the second recessed part 142 has a hexagonal shape, and the second coupling part 153 of the abutment 150 having the matching shape is inserted in the second recessed part 142, thereby preventing rotation of the abutment 150.

When the first coupling part 152 and the second coupling part 153 of the abutment 150 are respectively inserted in the first recessed part 141 and the second recessed part 142 of the first abutment coupling part 140, an abutment screw (not shown) passing through the penetration hole 151a of the abutment 150 is coupled to the screw hole 143. The screw hole 143 is manufactured to have the same size as the penetration hole 151a of the abutment 150.

Next, the first bone damage prevention part 170 and the first entrance guide part 160 formed at the opposite ends of the first body 120 are described below. The first bone damage prevention part 170 is formed at one end of the first body 120 to prevent an alveolar bone existing in an opening area of the drill hole H (refer to FIG. 3) due to the first continuous thread part 130 from being damaged when the first fixture 100 is implanted in the drill hole H.

The first bone damage prevention part 170 is formed in a non-threaded region where the first continuous thread part 130 is not formed, on an outer surface of the one end portion of the first body 120, to be integrally with the first body 120 by a predetermined length at the one end portion of the first body 120. In particular, the first bone damage prevention part 170 has a non-linear outer surface such that the diameter of the first bone damage prevention part 170 decreases from the one end portion of the first body 120 to the opposite side, as illustrated in an enlarged portion of FIG. 5.

As such, when the first bone damage prevention part 170 is provided at the one end portion of the first body 120 in a non-threaded region where the first continuous thread part 130 is not formed, an alveolar bone existing in the opening area of the drill hole H due to a thread part (not shown) formed to the one end portion of the first body 120 (the topside portion on the drawing sheet) as in the related art may be prevented from being damaged, leading a successful implant surgery. As illustrated in FIG. 1, a second bone damage prevention part 270 having the same structure and function as those of the first bone damage prevention part 170 is formed at the second fixture 200.

The first entrance guide part 160 is provided at the other end portion of the first body 120 opposite to the first bone damage prevention part 170. The first entrance guide part 160 is formed as long as a predetermined section in the lengthwise direction of the first body 120 from a leading end portion of the first body 120 with respect to a direction in which the first body 120 is implanted and guides the first body 120 in an initial implantation entrance direction.

If the first entrance guide part 160 is not formed like in the related art, that is, if the first continuous thread part 130 is formed even on the first entrance guide part 160, it may be difficult to initially insert the first body 120 due to the first continuous thread part 130. However, according to the present embodiment, when the first entrance guide part 160 is provided in a non-threaded region where the first continuous thread part 130 is not formed, the first entrance guide part 160 may be freely inserted into the drill hole H, and thus the implantation direction may be properly kept without distortion. Then, the first fixture 100 may be implanted by using the first continuous thread part 130. Therefore, implantation may be easily performed.

As described above, the first entrance guide part 160 may be provided in the non-threaded region where the first continuous thread part 130 is not formed in an area of the other end portion (a lower end portion on the drawing sheet) of the first body 120. The non-threaded region may be formed as a part of the first fixture 100 when the first fixture 100 is fabricated, or may be formed through a later process after the first continuous thread part 130 is formed in the entire region of the outer surface of the first body 120. The first entrance guide part 160 may be formed from the bottom side of the first body 120 to a position of the first body 120 spaced upward from the bottom side of the first body 120 by 1 mm to 3 mm.

The first entrance guide part 160 includes a first flat portion 161 which is horizontal flat, a first inclined portion 162 extending upward from a circumferential surface of the first flat portion 161 with an upwardly increasing radius, and a first rounded portion 163 connecting the first inclined portion 162 and the first continuous thread part 130 and having at least one area inwardly rounded toward the centerline of the first fixture 100. Unlike that shown in FIG. 4, the first rounded portion 163 and the first inclined portion 162 together form an arc line. As illustrated in FIG. 1, a second entrance guide part 260 having the same structure and function as those of the first entrance guide part 160 is formed in the second fixture 200.

On the other hand, the first continuous thread part 130 is formed in a spiral shape on an outer circumferential surface of the first body 120 so that the first fixture 100 may be implanted in a screw method. The first continuous thread part 130 in the first fixture 100 of the present embodiment is continuously formed on the outer surface of the first body 120.

In addition, a certain section of the thread part is discontinued on the outer surface of a conventional fixture (not shown), that is, the thread part does not continue, and one or a plurality of cutting edge portions are formed in the lengthwise direction of the body in the area. A sharp vertical leading end portion of the cutting edge portion may cause the fixture misaligned with a fixture implantation direction. However, in the first fixture 100 of the present embodiment, since the cutting edge portion does not exit, the first continuous thread part 130 that is continuous is formed on the outer surface of the first body 120. Thus, the misalignment of the first fixture 100 with the fixture implantation direction due to the first continuous thread part 130 may be prevented. In other words, the first continuous thread part 130 is continuously formed on the outer circumferential surface of the first body 120 except for the first bone damage prevention part 170 and the first entrance guide part 160. The same condition is applied to the second continuous thread part 230 of the second fixture 200. The shape and structural characteristics of the first continuous thread part 130 is described with reference to FIG. 8 with comparison with the second continuous thread part 230 of the second fixture 200.

As illustrated in FIG. 8, the first continuous thread part 130 includes a first leading end part 131*a* that is vertical or inclined toward one side, a first upper curved part 131*b* forming an upper surface of the first leading end portion 131*a*, and a first lower curved part 131*c* forming a lower surface of the first leading end part 131*a*. In detail, the shape of a thread of the first continuous thread part 130, that is, the shape of the first continuous thread part 130 of the present embodiment, is out of a typical shape of a triangular thread or a rectangular thread and processed such that the upper and lower surfaces thereof have a convex shape, not a linear shape, with respect to the first leading end part 131*a*.

In addition, the first leading end part 131*a* has a substantially vertical and linear shape, whereas the upper and lower portions with respect to the first leading end part 131*a* respectively form the first upper curved part 131*b* and the second lower curved part 131*c* having upwardly and downwardly convex shapes (concave viewed from the opposite side). Of course, any one of the first upper and lower curved parts 131*b* and 131*c* only may be formed. However, as in the present embodiment, the first upper and lower curved parts 131*b* and 131*c* may be provided symmetrically with respect to the first leading end part 131*a*. Such shape and structural characteristics may facilitate implantation of the first fixture 100 because a less resistance torque occurs during the implantation of the first fixture 100.

For reference, although an angle θ between imaginary straight lines (referred to dotted lines of FIG. 8) forming the first upper and lower curved parts 131*b* and 131*c* may be about 30°, the present invention is not limited thereto. Also, although in the above the first upper and lower curved parts 131*b* and 131*c* are illustrated and described to be symmetrical with each other, the first upper and lower curved parts 131*b* and 131*c* may have an asymmetrical shape. In this case, the first lower curved part 131*c* may be thicker. As a result, since it would suffice that the first upper and lower curved parts 131*b* and 131*c* facilitate implantation by reducing resistance torque during implantation of the first fixture 100, the angle between the first upper and lower curved parts 131*b* and 131*c* and the symmetrical or asymmetrical structure of the first upper and lower curved parts 131*b* and 131*c* may be appropriately changed according to a situation.

The second continuous thread part 230 of the second fixture 200 also has the same structure as the first continuous thread part 130 of the first fixture 100. In other words, the second continuous thread part 230 also includes a second leading end part 231*a*, and a second upper curved part 231*c* and a second lower curved part 231*c*, respectively forming upper and lower surfaces of the second leading end part 231*a*.

A pitch P between threads of the first continuous thread part 130 and a pitch P between threads of the second continuous thread part 230 are the same. An end portion region (a hatched portion ΔH of FIG. 8) of the second continuous thread part 230 is extended from the leading end part 131*a* of the first continuous thread part 130 further outwardly in a radius direction by a predetermined distance identically to the first upper and lower curved parts 131*b* and 131*c* of the first continuous thread part 130. In the above structure, the second fixture 200 may be implanted without additional drilling in the drill hole H (refer to FIG. 3) where the first fixture 100 was implanted and also without a damage to the alveolar bone therearound. Thus implant surgery may be conveniently performed compared to the related art.

For reference, in view of a contour line of the first continuous thread part 130, an imaginary contour line connecting the leading end portion of the first continuous thread part 130 from the first bone damage prevention part 170 to the first entrance guide part 160 forms a taper inclination line such that a width between the imaginary contour lines gradually decreases. This condition is identically applied to the second continuous thread part 230. Of course, the contour lines of the first continuous thread part 130 and the second continuous thread part 230 may have the same inclination throughout the entire area or only a partial section may have a tapered inclination. The condition may belong to a scope of rights of the present invention.

Finally, in short, in the implant system of the present embodiment with reference to FIG. 1, the first fixture 100 and the second fixture 200 have an almost common structure. In other words, the first body 120 of the first fixture 100 and the 220 of the second fixture 200 may be manufactured to be identical to each other and are common in that the first and second entrance guide parts 160 and 260 are provided at the first and second bone damage prevention parts 170 and 270.

However, in comparison between the first continuous thread part 130 of the first fixture 100 and the second continuous thread part 230 of the second fixture 200, the pitch P between threads of the first continuous thread part 130 and the pitch P between threads of the second continuous thread part 230 are identical to each other, whereas they are different in that the end portion region (the hatched portion ΔH of FIG. 8) of the second continuous thread part 230 is extended from the leading end part 131a of the first continuous thread part 130 further outwardly in a radius direction by a predetermined distance identically to the first upper and lower curved parts 131b and 131c of the first continuous thread part 130.

Thus, as described above, since the first body 120 of the first fixture 100 and the second body 220 of the second fixture 200 are equal, the drill hole H (refer to FIG. 3) may be formed in an alveolar bone by using the same drill (not shown). Also, when the first fixture 100 is implanted in the drill hole H (refer to FIG. 3) formed in an alveolar bone by using a common drill as shown in FIG. 1, although implantation of the first fixture 100 fails, the second fixture 200 may be directly implanted in the same drill hole H without having to enlarge the drill hole H or form another hole. Therefore, dental implantation may be easily performed as compared with the related art. This is possible since the first body 120 of the first fixture 100 is equal to the second body 220 of the second fixture 200 and only the sizes of the first and second continuous thread parts 130 and 230 are different from each other.

Referring to FIG. 2, for example, when the first fixture 100 having a thread diameter of 4.0 mm is implanted in the drill hole H (refer to FIG. 3) formed in an alveolar bone 13 with a common drill, although implantation of the first fixture 100 fails, the second fixture 200 having a thread diameter of 4.5 mm, for example, may be implanted in the same drill hole H without additional drilling. In addition, if implantation of the second fixture 200 fails, third and fourth fixtures having thread diameters of 5.0 mm and 5.5 mm may be implanted in the same drill hole H.

Based on the above description, an exemplary implant surgery will now be explained. First, a drill hole H as illustrated in FIG. 3 is formed by punching an implantation position by using a common drill (not shown). At this time, the diameter of the drill hole H may be similar or equal to a maximum width of the first body 120. Next, the first fixture 100 is placed toward the implantation position and inserted into the drill hole H (refer to FIG. 3) of the alveolar bone 13.

When the first fixture 100 is inserted in the drill hole H (refer to FIG. 3), since the first entrance guide part 160 of the first fixture 100 may be smoothly inserted in the drill hole H, the insertion direction of the first fixture 100 may not be distorted. In other words, since the direction of initial implantation may be easily guided, the implant surgery may be performed more easily and conveniently.

After the direction of implantation is set by the first entrance guide part 160, the first fixture 100 is implanted while being rotated. Then, the first continuous thread part 130 structurally facilitates implantation of the first fixture 100. When the implantation is completed, the first fixture 100 is fixed to the alveolar bone with a strong fixing force. In doing so, the first bone damage prevention part 170 located at the one end portion of the first fixture 100, that is, at the topside portion on the drawing sheet, prevents the alveolar bone existing in the opening area of the drill hole H from being damaged. On the other hand, although it is ideal to wait for a predetermined time after implanting the first fixture 100 as above, in some cases, implantation of the first fixture 100 may fail. In this case, the second fixture 200 may be directly implanted in the drill hole H (refer to FIG. 3) without additional drilling. As described above, this is possible since the first and second bodies 120 and 220 of the first and second fixtures 100 and 200 are equal. In particular, this is possible since the pitch P between threads of the first continuous thread part 130 and the pitch P between threads of the second continuous thread part 230 are identical to each other, whereas they are different in that the end portion region (the hatched portion ΔH of FIG. 8) of the second continuous thread part 230 is extended from the leading end part 131a of the first continuous thread part 130 further outwardly in a radius direction by a predetermined distance identically to the first upper and lower curved parts 131b and 131c of the first continuous thread part 130.

If the first fixture 100 is successfully implanted, after osseointegration of the first fixture 100, the abutment 150 (refer to FIG. 9) is coupled to the first abutment coupling part 140 of the first fixture 100.

When the abutment 150 is coupled to the first abutment coupling part 140, the first coupling part 152 and the second coupling part 153 of the abutment 150 are inserted into and coupled to the first recessed part 141 and the second recessed part 142 of the first abutment coupling part 140, respectively. Then, rotation of the abutment 150 is prevented by the coupling between the second coupling part 153 of the abutment 150 and the second recessed part 142 of the first abutment coupling part 140. In addition, owing to strong or tight coupling between the first coupling part 152 of the abutment 150 and the first recessed part 141 of the first abutment coupling part 140, the abutment 150 may not be easily detached, and the possibility of infection may be reduced owing to reliable sealing formed by the strong or tight coupling.

After the first coupling part 152 and the second coupling part 153 of the abutment 150 are respectively inserted in the first recessed part 141 and the second recessed part 142 of the first abutment coupling part 140, an abutment screw (not shown) is inserted in the penetration hole 151a of the abutment 150 and is coupled to the screw hole 143 of the first abutment coupling part 140. Then, the implant surgery is completed by attaching a prosthesis to the abutment 150.

As described above, according to the implant system of the present embodiment, although implantation of the first fixture 100 fails, the second fixture 200 may be directly implanted without additional drilling. Therefore, dental implantation may be conveniently performed as compared with the related art.

In addition, according to the first and second fixtures 100 and 200 for dental implants according to the present embodiment, the alveolar bone existing in the opening area of the drill hole H may be prevented from being damaged due to the thread part (not shown) formed throughout the entire outer surface of the body in a conventional fixture. Thus, dental implantation may be performed more conveniently.

Although embodiments have been described with reference to a number of illustrative embodiments thereof, it should be understood that numerous other modifications and embodiments may be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

The present invention may be applied to the field of a dental implant surgery.

What is claimed are:

1. A dental implant fixture comprising:
 a body;
 a continuous thread part including a continuous thread continuously formed in a spiral shape along an outer circumferential direction of the body;
 a bone damage prevention part formed at one end portion of the body and configured to be capable of preventing an alveolar bone existing in an opening area of a hole where the dental implant fixture is implanted from being damaged due to the continuous thread part; and
 an entrance guide part provided in a non-threaded region at the other end portion of the body, having a length of 1 mm to 3 mm in a lengthwise direction of the body and guiding the body in an initial implantation entrance direction,
 wherein the entrance guide part comprises:
 a flat portion forming a flat surface perpendicular to the lengthwise direction of the body;
 an inclined portion extending toward the one end portion of the body from the flat portion, a radius of the inclined portion gradually increasing toward the one end portion of the body; and
 a rounded portion connecting the inclined portion and the continuous thread part, a radius of the rounded portion being larger than the radius of the inclined portion, and having at least one area inwardly rounded toward a centerline of the fixture.

2. The dental implant fixture according to claim 1, wherein the bone damage prevention part has a non-linear outer surface such that a diameter of the bone damage prevention part decreases towards the other end portion of the body.

3. The dental implant fixture according to claim 1, wherein an outside of the body is tapered in a manner such that a diameter of the body decreases along an implantation direction, and
 an imaginary contour line connecting a leading end portion of the continuous thread forms a taper inclination line.

4. The dental implant fixture according to claim 1, wherein the continuous thread comprises:
 a leading end portion; and
 a curved part forming an upper surface and a lower surface of the continuous thread and reducing resistance torque.

5. The dental implant fixture according to claim 4, wherein the upper surface includes an inwardly-curved upper surface and the lower surface includes an inwardly-curved lower surface.

6. The dental implant fixture according to claim 1, wherein an abutment coupling part to which an abutment is coupled is provided in an inner area of the one end portion of the body, and the abutment coupling part comprises:
 a first recessed part primarily recessed from one end of the body in the lengthwise direction of the body;
 a second recessed part secondarily recessed from a bottom surface of the first recessed part in the lengthwise direction of the body and having a polygonal shape; and
 a screw hole formed in a center region of the second recessed part in the lengthwise direction of the body, to which an abutment screw for coupling the abutment is coupled.

\* \* \* \* \*